United States Patent [19]

Ostersehlt et al.

[11] Patent Number: 4,514,413
[45] Date of Patent: Apr. 30, 1985

[54] GASTRIC ACID SECRETION INHIBITING N-(IMIDAZOL-1-YLALKYL)THIOUREA DERIVATIVES

[75] Inventors: Bernd Ostersehlt, Ludwigshafen; Albrecht Franke, Wachenheim; Fritz-Frieder Frickel, Deidesheim; Marco Thyes, Ludwigshafen; Ludwig Friedrich, Bruehl; Josef Gries, Wachenheim; Dieter Lenke, Ludwigshafen, all of Fed. Rep. of Germany

[73] Assignee: BASF Aktiengesellschaft, Fed. Rep. of Germany

[21] Appl. No.: 482,790

[22] Filed: Apr. 7, 1983

[30] Foreign Application Priority Data

Apr. 10, 1982 [DE] Fed. Rep. of Germany ....... 3213509

[51] Int. Cl.³ .................. A61K 31/415; C07D 233/61
[52] U.S. Cl. ..................... 514/397; 548/336
[58] Field of Search ................ 548/336; 424/273 R

[56] References Cited

U.S. PATENT DOCUMENTS

| | | | |
|---|---|---|---|
| 3,876,647 | 4/1975 | Durant et al. | 260/294.8 G |
| 3,897,444 | 7/1975 | Durant et al. | 260/306.8 R |
| 3,975,530 | 8/1976 | Durant et al. | 424/270 |
| 3,978,075 | 8/1976 | Toth et al. | 260/309.2 |
| 4,226,874 | 10/1980 | Durant et al. | 424/269 |
| 4,233,302 | 11/1980 | Martin-Smith | 424/273 R |
| 4,279,911 | 7/1981 | Martin-Smith | 424/273 R |
| 4,304,780 | 12/1981 | Martin-Smith | 424/273 R |
| 4,386,211 | 5/1983 | Henderson | 548/336 |

FOREIGN PATENT DOCUMENTS

| | | |
|---|---|---|
| 1338169 | 11/1973 | United Kingdom . |
| 1397436 | 6/1975 | United Kingdom . |
| 1398426 | 6/1975 | United Kingdom . |
| 2016011 | 9/1979 | United Kingdom . |
| 2067991 | 8/1981 | United Kingdom . |

OTHER PUBLICATIONS

R. N. Brogden et al., Drugs 24 (1982), 267-303.
G. J. Durant et al., J. Med. Chem. 20 (1977), 901.

Primary Examiner—Henry R. Jiles
Assistant Examiner—Kurt G. Briscoe
Attorney, Agent, or Firm—Keil & Weinkauf

[57] ABSTRACT

N-substituted imidazole derivatives of the formula I

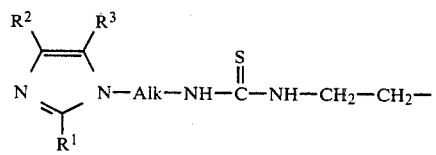

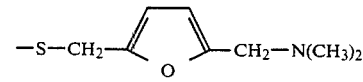

where $R^1$, $R^2$ and $R^3$ are identical or different and are each hydrogen or alkyl with 1 or 3 carbon atoms and Alk is an alkylene chain of 2 to 4 carbon atoms, and their salts with physiologically tolerated acids, processes for their preparation, drugs containing a compound of the formula I or one of its salts, and their use for treating disorders associated with gastric hyperacidity.

7 Claims, No Drawings

GASTRIC ACID SECRETION INHIBITING N-(IMIDAZOL-1-YLALKYL)THIOUREA DERIVATIVES

Histamine $H_2$ antagonists are useful in the treatment of disorders associated with pathologically increased gastric secretion. Examples of known histamine $H_2$ antagonists are ranitidine, metiamide and cimetidine (cf. for example, R. N. Brogden et al, "Ranitidine: A review of its pharmacology and therapeutic use in peptic ulcer disease and other allied diseases", Drugs 24 (1982), 267–303; G. J. Durant and C. R. Ganellin et al, J. Med. Chem. 20 (1977), 901; and German Published Application DAS No. 2,344,779, Belgian Pat. No. 779,775 and U.S. Pat. Nos. 3,975,530, 3,876,647 and 3,897,444). However, in many cases their activity is not satisfactory.

It is an object of the present invention to remedy this deficiency.

We have found that this object is achieved by N-substituted imidazole derivatives of the formula I

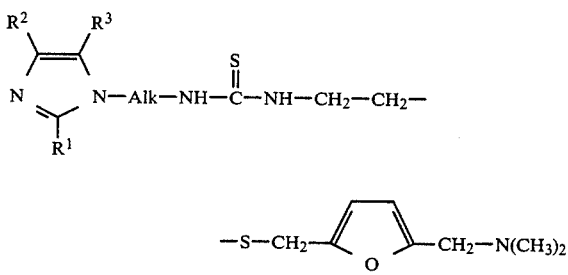

where $R^1$, $R^2$ and $R^3$ are identical or different and are each hydrogen or alkyl of 1 to 3 carbon atoms and Alk is an alkylene chain of 2 to 4 carbon atoms, and their salts with physiologically tolerated acids.

Examples of alkylene chains Alk are ethylene, propylene and butylene, propylene being preferred.

Examples of novel compounds of the formula (I) are:

N-[3-(imidazol-1-yl)-propyl]-N'-{2-[[5-(N,N-dimethylaminomethyl)-furan-2-yl]-methylthio]-ethyl}-thiourea N-[3-(2-methylimidazol-1-yl)-propyl]-N'-{2-[[5-(N,N-dimethylaminomethyl)-furan-2-yl]-methylthio]-ethyl}-thiourea 2-[3-(2-ethylimidazol-1-yl)-propyl]-N'-{2-[[5-(N,N-dimethylaminomethyl)-furan-2-yl]-methylthio]-ethyl}-thiourea N-[3-(2-propylimidazol-1-yl)-propyl]-N'-{2-[[5-(N,N-dimethylaminomethyl)-furan-2-yl]-methylthio]-ethyl}-thiourea, N-[3-(2-isopropylimidazol-1-yl)-propyl]-N'-{2-[[5-(N,N-dimethylaminomethyl)-furan-2-yl]-methylthio]-ethyl}-thiourea N-[3-(4-methylimidazol-1-yl)-propyl]-N'-{2-[[5-(N,N-dimethylaminomethyl)-furan-2-yl]-methylthio]-ethyl}-thiourea N-[3-(5-methylimidazol-1-yl)-propyl]-N'-{2-[[5-(N,N-dimethylaminomethyl)-furan-2-yl]-methylthio]-ethyl}-thiourea N-[3-(2,4-dimethylimidazol-1-yl)-propyl]-N'-{2-[[5-(N,N-dimethylaminomethyl)-furan-2-yl]-methylthio]-ethyl}-thiourea N-[3-(2,5-dimethylimidazol-1-yl)-propyl]-N'-{2-[[5-(N,N-dimethylaminomethyl)-furan-2-yl]-methylthio]-ethyl}-thiourea N-[3-(4,5-dimethylimidazol-1-yl)-propyl]-N'-{2-[[5-(N,N-dimethylaminomethyl)-furan-2-yl]-methylthio]-ethyl}-thiourea N-[3-(2-ethyl-4-methylimidazol-1-yl)-propyl]-N'-{2-[[5-(N,N-dimethylaminomethyl)-furan-2-yl]-methylthio]-ethyl}-thiourea N-[3-(2-ethyl-5-methylimidazol-1-yl)-propyl]-N'-{2-[[5-(N,N-dimethylaminomethyl)-furan-2-yl]-methylthio]-ethyl}-thiourea N-[3-(2,4,5-trimethylimidazol-1-yl)-propyl]-N'-{2-[[5-(N,N-dimethylaminomethyl)-furan-2-yl]-methylthio]-ethyl}-thiourea N-[2-(2-methylimidazol-1-yl)-ethyl]-N'-{2-[[5-(N,N-dimethylaminomethyl)-furan-2-yl]-methylthio]-ethyl}-thiourea N-[2-(2-ethylimidazol-1-yl)-ethyl]-N'-{2-[[5-(N,N-dimethylaminomethyl)-furan-2-yl]-methylthio]-ethyl}-thiourea N-[4-(2-methylimidazol-1-yl)-butyl]-N'-{2-[[5-(N,N-dimethylaminomethyl)-furan-2-yl]-methylthio]-ethyl}-thiourea N-[4-(2-ethylimidazol-1-yl)-butyl]-N'-{2-[[5-(N,N-dimethylaminomethyl)-furan-2-yl]-methylthio]-ethyl}-thiourea Examples of physiologically tolerated organic or inorganic acids for salt formation are hydrochloric acid, hydrobromic acid, phosphoric acid, sulfuric acid, oxalic acid, maleic acid, fumaric acid, lactic acid, tartaric acid, malic acid, citric acid, salicylic acid, adipic acid and benzoic acid. Further suitable acids are to be found in Fortschritte der Arzneimittelforschung, Volume 10, pages 224–225, Birkhauser Verlag, Basle and Stuttgart, 1966.

The present invention also relates to a process for the preparation of the compounds of the formula I, wherein (a) a thio compound of the formula II $$(H_3C)_2N-CH_2-\underset{O}{\underset{|}{\diagup\!\!\!\diagdown}}-CH_2-S-C_2H_4-NH-\overset{S}{\overset{\|}{C}}-S-Y \quad (II)$$

where Y is $C_1$–$C_4$-alkyl or aralkyl, is reacted with an ω-aminoalkylimidazole of the general formula III $$\begin{array}{c} R^2 \quad R^3 \\ \diagdown\!=\!\diagup \\ N \quad N-Alk-NH_2 \\ \diagdown\!\diagup \\ | \\ R^1 \end{array} \quad (III)$$

where $R^1$, $R^2$ and $R^3$ have the above meanings, or (b) 2-[[5-(N,N-dimethylaminomethyl)-furan-2-yl]-methylthio]ethylamine is reacted with a compound of the formula IV $$\begin{array}{c} R^2 \quad R^3 \\ \diagdown\!=\!\diagup \\ N \quad N-Alk-N\overset{S}{\underset{H}{\diagdown}}\!\!\!\diagup\!SY \\ \diagdown\!\diagup \\ | \\ R^1 \end{array} \quad (IV)$$

where $R^1$, $R^2$, $R^3$, Alk and Y have the above meanings, or (c)  2-[[5-(N,N-dimethylaminomethyl)-furan-2-yl]-methylthio]-ethylamine is reacted with a compound of the formula V

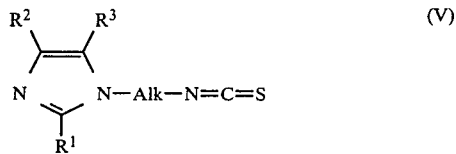

where $R^1$, $R^2$, $R^3$ and Alk have the above meanings, and, if required, the resulting compound is converted to its salts with physiologically tolerated acids.

The reaction described under (a) is carried out at room temperature or at elevated temperatures, advantageously at from 50° to 120° C., under atmospheric pressure, or under superatmospheric pressure in a closed vessel, if required the mixture being heated at the stated temperature. This reaction is particularly successful where Y is methyl.

The starting compounds can be reacted directly, ie. without the addition of a diluent or solvent, but it is advantageous to carry out the reaction in the presence of an inert diluent or solvent, for example a lower alcohol of 1 to 4 carbon atoms, eg. methanol, ethanol or propanol, a lower saturated dialkyl ether, dialkylglycol ether or cyclic ether, eg. diethyl ether, 1,2-dimethoxyethyl glycol ether, tetrahydrofuran or dioxane, a dialkylformamide, eg. dimethylformamide or diethylformamide, or dimethylsulfoxide, acetonitrile or water, or a mixture of these solvents.

The most suitable solvents are lower alcohols, preferably methanol or ethanol, and water.

The reaction is preferably carried out at from 50° to 120° C., under atmospheric pressure.

The overall reaction depends on the reaction temperature, and is in general complete in the course of from 2 to 25 hours. The product can be isolated in a conventional manner, for example by filtration or by distilling off the diluent or solvent from the reaction mixture, and can be purified in a conventional manner, for example by recrystallization from a solvent, conversion to a salt of a physiologically tolerated acid or column chromatography.

The reaction of process (b), ie. the nucleophilic substitution of SY, is carried out as described above for the reaction of a thio compound of the general formula (II) with an alkylaminoimidazole of the general formula (III).

Reaction (c) is carried out in the presence of a solvent, for example a lower alcohol of 1 to 4 carbon atoms, preferably methanol, ethanol or isopropanol, a dialkylformamide, eg. dimethylformamide or diethylformamide, or dimethylsulfoxide or water, preferably at from 0° to 100° C., under atmospheric pressure.

The product is isolated as described in (a).

The starting materials of the formulae II, III, IV and V are known from the literature, or can be prepared by a conventional process.

Finally, the present invention relates to drugs which in addition to conventional carriers and diluents contain, as the active compound, a compound of the formula I or its physiologically tolerated salt.

The novel compounds can be administered in a conventional manner, preferably orally or intravenously.

The dosage depends on the age, condition and weight of the patient and on the route of administration. As a rule, the daily dose of active compound is from about 0.5 to 20 mg/kg of body weight for oral administration and from 0.05 to 10 mg/kg of body weight for intravenous administration. In particular cases, however, it may be necessary to increase the doses.

The novel compounds and their physiologically tolerated addition salts with acids possess useful pharmacological properties, and are suitable for the treatment of disorders associated with pathologically increased gastric secretion, for example gastric ulcers and duodenal ulcers.

The histamine $H_2$ receptor-blocking action was demonstrated by the following methods:

In male Sprague-Dawley rats (weight 210–310 g) which have been anesthetized with urethane (1.78 g/kg, administered intravenously), the specific $H_2$ receptor agonist dimaprit (S-[3-(N,N-dimethylamino)-propyl]-isothiourea; cf. PARSONS, M. E. et al., Agents and Actions 7, (1977), 31–37, and FLYNN, Sh. B. et al., Brit. J. Pharmacol. 61 (1977), 101–107), when injected intravenously in a dose of 3.16 mg, induces an average lowering of the blood pressure by 27±0.7 mm Hg at initial pressures of 100±1.1 mm Hg (number of animals N=70). $H_2$ receptor antagonists, eg. cimetidine or ranitidine, effect specific and dose-dependent inhibition of this dimaprit-induced lowering of the blood pressure. The substances tested were administered intravenously 5 minutes before the dimaprit injection. The ED 50% is determined as the dose which inhibits the dimaprit-induced lowering of the blood pressure by 50% (Table 1).

Inhibition of the secretion of gastric acid results in an increase in the pH of the gastric mucus membrane. This is investigated on groups of 5 conscious female Sprague-Dawley rats weighing 160–180 g. The animals receive no food for 48 hours (water ad libitum), and are pretreated subcutaneously with various doses of the test substances. After 1 hour, they are anesthetized intravenously with 46.4 mg/kg of Na hexobarbital. A pH electrode (Philips Special Electrode Type CJP) is then introduced into the stomach, and the pH at the surface of the gastric mucus membrane is measured (pH of untreated animals: 1.40±0.02; N=200). The dose which increases the pH by 0.75 on average compared with untreated control animals is determined, as the ED 0.75, from the linear regression between the logarithms of the applied doses and the increase in the pH (Table 2).

The experiments (Table 1) show that the novel compounds strongly inhibit the dimaprit-induced lowering of the blood pressure. The action is superior to that of the known $H_2$ receptor antagonist cimetidine by a factor of from 10 to 26. Compared with ranitidine, too, the effective dose is the same or up to 2.5 times smaller.

The compounds according to the invention inhibit the secretion of gastric acid, this inhibition being evident in a dose-dependent increase in the pH at the surface of the gastric mucous membrane (Table 2).

In this respect, the compound of Example 1 is 8.7 times more effective than the known drug cimetidine, and 1.7 times more effective than ranitidine. Furthermore, the substances inhibit the formation of gastric ulcers.

TABLE 1

Inhibition of the dimaprit-induced lowering of the blood pressure

| Substance | ED 50%* | R.A.** |
|---|---|---|
| Example No. 1 | 0.092 | 23.91 |
| Example No. 2 | 0.10 | 22.00 |
| Example No. 3 | 0.17 | 12.94 |
| Example No. 4 | 0.22 | 10.00 |
| Example No. 8 | 0.084 | 26.19 |
| Example No. 9 | 0.22 | 10.00 |
| Ranitidine | 0.21 | 10.48 |
| Cimetidine | 2.2 | 1.00 |

Rat, urethane anesthesia, intravenous administration

*ED 50% = dose which inhibits the dimaprit-induced lowering of the blood pressure by 50%
**R.A. = relative activity; cimetidine = 1.00

TABLE 2

Inhibition of the gastric secretion in the rat

| Substance | ED 0.75 | R.A. |
|---|---|---|
| Example No. 1 | 0.052 | 8.65 |
| Cimetidine | 0.45 | 1.00 |
| Ranitidine | 0.086 | 5.23 |

Subcutaneous administration; R.A. = relative activity

The novel compounds may be employed in the conventional solid or liquid pharmaceutical forms, such as tablets, capsules, powders, granules, coated tablets or solutions. These are prepared in a conventional manner, and to do so the active compounds can be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. L. G. Goodman and A. Gilman, The Pharmacological Basis of Therapeutics). The formulations thus obtained normally contain from 0.1 to 99% by weight of the active compound.

EXAMPLE 1

3.6 g of 3-[1-(2-methylimidazolyl)]-propyl isothiocyanate are dissolved in 40 ml of methanol, 4.3 g of 2-[[5-(N,N-dimethylaminomethyl)-furan-2-yl]-methylthio]-ethylamine are added and the mixture is left to stand overnight and then evaporated down. The residue is chromatographed with dichloromethane over aluminum oxide, and the resulting oil is crystallized with oxalic acid. 6.5 g (57% of theory) of N-[3-(2-methylimidazol-1-yl)-propyl]-N'-{2-[[5-(N,N-dimethylaminomethyl)-furan-2-yl]-methylthio]-ethyl}-thiourea dioxalate of melting point 126° C. are obtained.

$C_{18}H_{29}ON_5S_2.2(COOH)_2 \times 0.5H_2O(585)$

Calculated: 45.1 C 5.8 H 12.0 N 10.9 S; Found: 44.8 C 5.9 H 12.0 N 10.8 S.

EXAMPLE 2

2.6 g of N-3-(2-isopropylimidazol-1-yl)-propyl S-methyl dithiocarbamate and 2.1 g of 2-[[5-(N,N-dimethylaminomethyl)-furan-2-yl]-methyl]-ethylamine in 100 ml of water are stirred for 24 hours at 80° C., 50 ml of methanol are added and the mixture is then stirred for 6 hours with 3 g of active carbon. The solution is filtered, and the filtrate is evaporated to dryness under reduced pressure. 3.1 g (72% of theory) of N-[3-(2-isopropylimidazol-1-yl)-propyl]-N'-{2-[[5-(N,N-dimethylaminomethyl)-furan-2-yl]-methylthio]-ethyl}-thiourea are obtained as a colorless oil.

$C_{20}H_{33}N_5S_2O \times 0.75H_2O(438)$

Calculated: 55.0 C 7.9 C 16.0 N 14.6 S; Found: 55.2 C 8.0 C 16.1 N 14.0 S.

EXAMPLE 3

3.0 g of N-{2-[[5-(N,N-dimethylaminomethyl)-furan-2-yl]-methylthio]-ethyl}S-methyl dithiocarbamate and 1.5 g of 1-(3-aminopropyl)-2-ethylimidazole in 100 ml of H₂O are stirred for 24 hours at 80° C., the mixture is then evaporated down, and the residue is chromatographed with dichloromethane over aluminum oxide. The eluate is evaporated down, and the residue is crystallized with oxalic acid. 3.5 g (59% of theory) of N-[3-(2-ethylimidazol-1-yl)-propyl]-N'-{2-[[5-(N,N-dimethylaminomethyl)-furan-2-yl]-methylthio]-ethyl}-thiourea dioxalate of melting point 137° C. are obtained. $C_{23}H_{35}O_9N_5S_2$ (590)

Calculated: 46.9 C 6.0 H 11.9 N 10.9 S; Found: 46.7 C 5.8 H 11.7 N 11.0 S.

The compounds shown in the Table below are prepared from N-{2-[[5-(N,N-dimethylaminomethyl)-furan-2-yl]-methylthio]-ethyl}S-methyl dithiocarbamate and the corresponding 1-(aminoalkyl)-imidazole by the procedure described in Example 3. In each case, the residue obtained on evaporation to dryness was chromatographed with dichloromethane over aluminum oxide.

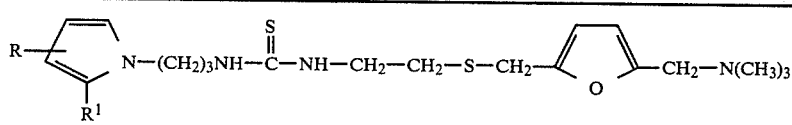

| Example No. | R | Melting point [°C.] | Yield [% of theory] | Salt (hydrate form) | Analysis | | | | Name |
|---|---|---|---|---|---|---|---|---|---|
| 4 | 2-C₃H₇ | 100 | 53 | 2(COOH)₂ | 47.7 C | 6.2 H | 1.6 N | 10.6 S | N—[3-(2-propylimidazol-1-yl)-propyl]- |
| | | | | | 47.3 C | 6.2 H | 11.3 N | 10.4 S | N'—{2[[5-(N,N.—dimethyl aminomethyl)-furan-2-yl[- methylthio]-ethyl}-thiourea |
| 5 | 4-CH₃ | 136 | 47 | 2(COOH)₂ | 45.9 C | 5.8 H | 12.2 N | 11.1 S | N—[3-(4-methylimidazol-1-yl)-propyl]- |
| | | | | | 45.7 C | 5.8 H | 11.8 N | 11.4 S | N'—{2-[[5-(N,N—dimethylaminomethyl)-furan-2-yl]-methylthio]-ethyl}-thiourea |
| 6 | 4,5-di-CH₃ | 156 | 40 | 2(COOH)₂ | 46.8 C | 6.0 H | 11.9 N | 10.9 S | N—[3-(4,5-dimethylimidazol-1-yl)-propyl]-N'—{2-[[5-N,N—dimethyl- |
| | | | | | 46.3 C | 6.0 H | 1.8 N | 10.4 S | |

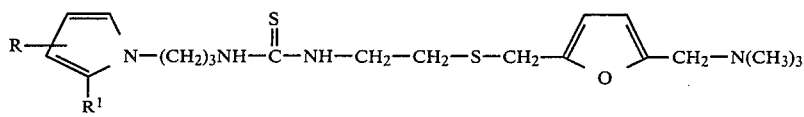

| Example No. | R | Melting point [°C.] | Yield [% of theory] | Salt (hydrate form) | Analysis | | | | Name |
|---|---|---|---|---|---|---|---|---|---|
| 7 | 5-CH₃ | 157 | 73 | 2(COOH)₂ | 45.9 C | 5.8 H | 12.2 N | 11.1 S | N—[5-(5-methylimidazol-1-yl)-propyl]- |
|   |   |   |   |   | 45.3 C | 5.7 H | 12.0 N | 10.9 S | N'—{2-[[5-N,N—dimethylaminomethyl)-furan-2-yl]-methylthio]-ethyl}-thiourea |
| 8 | 2,4,5-tri-CH₃ | amorphous | 31 | 0.5 CH₃OH | 54.8 C | 8.0 H | 15.6 N | 14.3 S | N—[3-(2,4,5-trimethylimidazol-1-yl)- |
|   |   |   |   | 0.5 H₂O | 54.3 C | 7.9 H | 15.5 N | 14.5 S | propyl]-N'—{2-[[5-(N,N—dimethylaminomethyl)-furan-2-yl]-methylthio]-ethyl}-thiourea |
| 9 | 2-C₂H₅; 5-Me | 123 | 58 | 2(COOH)₂ | 47.7 C | 6.2 H | 11.6 N | 10.6 S | N—[3-(2-ethyl-5-methylimidazol-1-yl)- |
|   |   |   |   |   | 47.3 C | 6.2 H | 11.3 N | 10.4 S | propyl]-N'—{2-[[5-N,N—dimethylaminomethyl)-furan-2-yl]-methylthio]-ethyl}-thiourea |

We claim:

1. An N-substituted imidazole derivative of the formula I

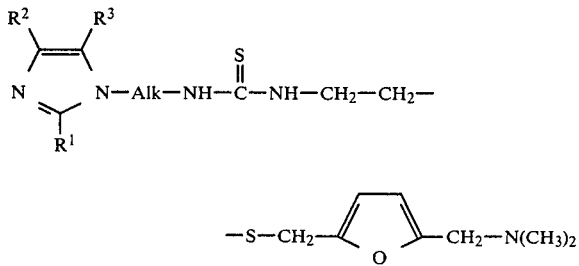

where $R^1$, $R^2$ and $R^3$ are identical or different and are each hydrogen or alkyl of 1 to 3 carbon atoms and Alk is an alkylene chain of 2 to 4 carbon atoms, and its salts with physiologically tolerated acids.

2. N-[3-(2-Methylimidazole-1-yl)-propyl]-N'-{2-[[5-(N,N-dimethylaminomethyl)-furan-2-yl]-methylthio]-ethyl}-thiourea.

3. N-[3-(2-ethylimidazol-1-yl)-propyl]-N'-{2-[[5-(N,N-dimethylaminomethyl)-furan-2-yl]-methylthio]-ethyl}-thiourea.

4. N-[3-(2-Propylimidazol-1-yl)-propyl]-N'-{2-[[5-(N,N-dimethylaminomethyl)-furan-2-yl]-methylthio]-ethyl}-thiourea.

5. N-[3-(2,4,5-Trimethylimidazol-1-yl)-propyl]-N'-{2-[[5-(N,N-dimethylaminomethyl)-furan-2-yl]-methylthio]-ethyl}-thiourea.

6. A compound selected from the group consisting of N-[3-(4,5-dimethylimidazol-1-yl)-propyl]-N'-{2-[[5-(N,N-dimethylaminomethyl)-furan-2-yl]-methylthio]-ethyl}-thiourea, N-[3-(2-ethyl-5-methylimidazol-1-yl)-propyl]-N'-{2-[[5-(N,N-dimethylaminomethyl)-furan-2-yl]-methylthio]-ethyl}-thiourea, N-[3-(5-methylimidazol-1-yl)-propyl]-N'-{2-[[5-(N,N-dimethylaminomethyl)-furan-2-yl]-methylthio]-ethyl}-thiourea, N-[3-(4-methylimidazol-1-yl)-propyl]-N'-{2-[[5-(N,N-dimethylaminomethyl)-furan-2-yl]-methylthio]-ethyl}-thiourea and N-[3-(2-i-propylimidazol-1-yl)-propyl]-N'-{2-[[5-(N,N-dimethylaminomethyl)-furan-2-yl]-methylthio]-ethyl}-thiourea.

7. A composition for treating disorders associated with gastric hyperacidity which comprises a pharmaceutically acceptable carrier and/or diluent and an amount of a compound of the formula I as set forth in claim 1, effective to inhibit the secretion of gastric acid, or one of its physiologically tolerated salts.

* * * * *